June 27, 1939. J. PROIETTI Plant Pat. 333
ROSE
Filed Feb. 7, 1938
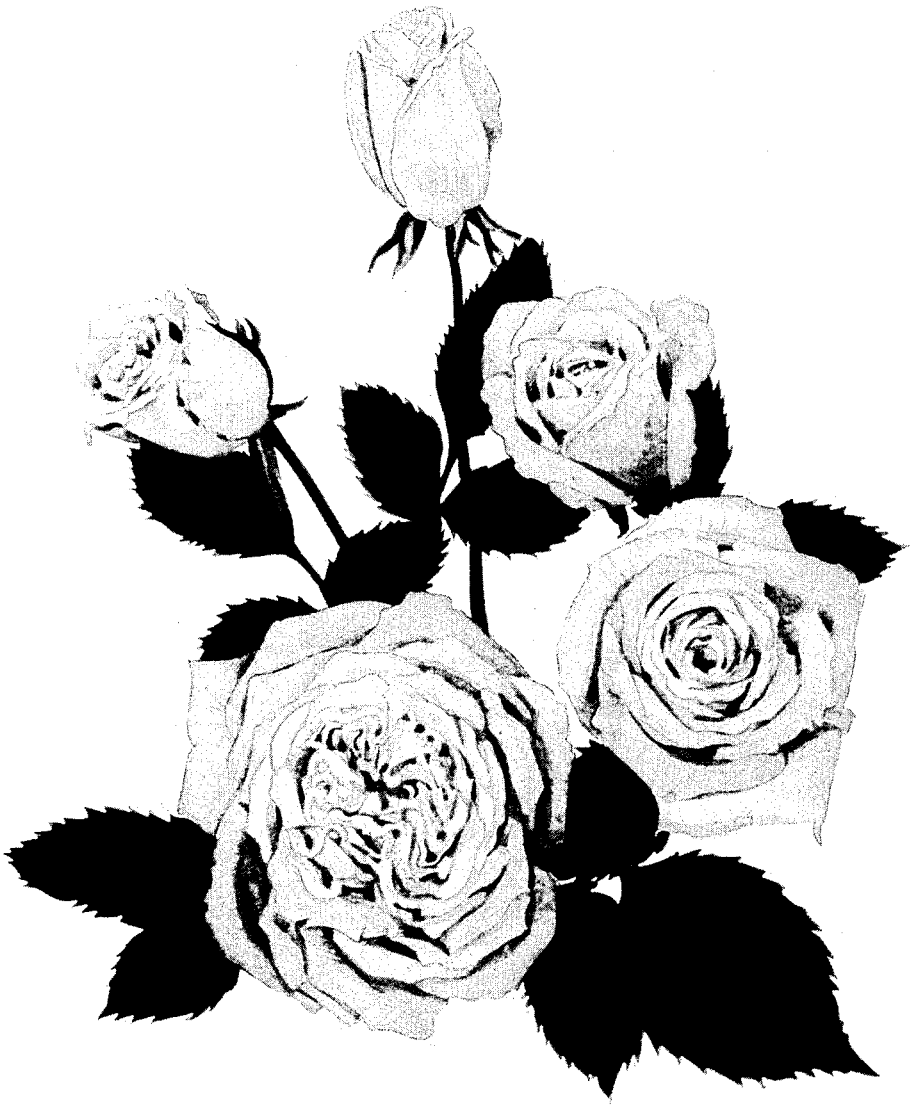
INVENTOR
JOSEPH PROIETTI
BY Boyken & Mohler
ATTORNEYS Patented June 27, 1939

Plant Pat. 333

UNITED STATES PATENT OFFICE

333

ROSE

Joseph Proietti, San Leandro, Calif.

Application February 7, 1938, Serial No. 189,034

1 Claim. (Cl. 47—61)

This invention relates to roses, and the object of the invention is to produce a rose having a new and improved color, which rose is hardy, and produces relatively large buds and blossoms. Other objects will appear in the specification attached hereto.

The colored illustrations accompanying this application show the buds and blossoms, foliage and stems, the blossoms being in the several stages of development succeeding the stage in which the bud is tight with the sepals enclosing the same.

This rose and plant were developed at San Leandro, California, from cross-pollinization of the Hollywood on the Dame Edith Helen, and is asexually reproduced as a distinct new variety of bush rose by budding. The varietal characteristics which distinguish my rose from the Dame Edith Helen and Hollywood have been observed upon buds or plants reproduced by budding. The buds are relatively long and slender and the petals open out into a relatively large flower in which the color is uniformly distributed over the petals, the upper sides of which are most closely described as being of a relatively deep and clear rose madder tendency toward purple madder with the under sides of the petals being of substantially the same color, but lighter. This color is noticeably darker than the Dame Edith Helen and noticeably lighter than the Hollywood, and is readily distinguishable over either of said varieties. The buds open perfectly into a full bloom and the plant has a greater production of blossom than the Dame Edith Helen.

In the foregoing general description and in the following more detailed description, the colors designated were taken from the color charts identified in the publication "Specimen Tints of Artists' Colors", published by Winsor & Newton, Ltd., London (1927).

*Parentage.*—Hollywood on Dame Edith Helen, by cross pollinization.

*Classification.*—Bush rose.

*Flower*

*Blooming habit.*—Seasonal in open, everblooming in greenhouse.

*Bud*

*Size.*—Large.

*Form.*—Pointed and slender.

*Color.*—Relatively deep Rose Madder tending toward Purple Madder on inside of petals and lighter Rose Madder on outside of petals.

*Color of sepals.*—Middle cinnabar green on outside and same green but whitish on inside; shape: ovate—lanceolate at base, long attenuate at apex with few to several long slender teeth at edges; position: turned forward over petals in tight bud, and turned abruptly backward when bud commences to loosen.

*Calyx.*—Shape: short campanulate; size: relatively small; aspect: smooth.

*Peduncle.*—Medium to long with widely scattered small, weak prickles.

*Opening.*—Opens well.

*Bloom*

*Size.*—Medium to large (4 to 5 inches).

*Borne.*—Singly or with one or two accessory blossoms borne several inches below the terminal one.

*Stems.*—Medium but sturdy.

*Form.*—Rounded when open.

*Petalage.*—55 to 75, innermost small and crowded.

*Color.*—Deep, clear rose madder inside tending toward purple madder. Holds color well with age and does not noticeably change from time in bud until petals fall. Color covers full petal uniformly, except at base where tone shades through white to yellow at tip of base. Pencillings on the petals are darker but of generally the same color as the remainder of petals. Outer sides of petals lighter than inside but same general color.

*Texture.*—Firm and strong but not heavy.

*Appearance.*—Inside velvety, outside smooth and soft and slightly metallic.

*Form.*—Rather full ovate—acuminate with point where attached to calyx, and outer edges slightly crinkled and irregular.

*Arrangement.*—Petals uniformly disposed, except in center where they are crowded.

*Persistence.*—Drop off cleanly.

*Fragrance.*—Pronounced and rich.

*Lastingness.*—Greater than average, blooms last five to eight days.

*Genital Organs*

*Stamen filaments.*—Yellow with pinkish cast.

*Anthers.*—Reddish brown.

*Pollen.*—Yellow.

*Styles.*—A tufted group, light yellow with reddish streaks.

*Stigmas.*—Light yellow.

*Ovaries.*—Some normal, others abortive.

*Plant*

*Form.*—Growth active and sturdy.

*Foliage.*—Size, medium; quantity, moderate. Color, mature foliage; deep cinnabar green with brownish red edges on leaves nearest flowers; below, terre verte green with purplish cast. Shape—ovate. Texture—firm but soft. Edge—serrate.

*Leaf stem.*—Color light Hooker's Green on underside and darker green on upper side with reddish brown overlay. One to several light thorns below with weak prickles above. Stipules, small, slender and pointed.

*Thorns.*—Quantity—moderate and fewer on flower bearing stems. Form—relatively short, base thin and narrow, point sharp and slender, definitely re-curved. Color—brownish base, green tips. Position—irregular ½ to 3 inches or more apart.

Having described my rose, I claim:

The new variety of rose as disclosed, characterized by a bush plant producing relatively large, double flowers which flowers are darker in color than that of the Dame Edith Helen and lighter in color than that of the Hollywood, which color is substantially a relatively deep rose madder tending toward purple madder, said flowers being from about 4 to about 5 inches in breadth when in full bloom and of the color and character resulting from a bush rose produced by cross-pollinization of a Hollywood on a Dame Edith Helen.

JOSEPH PROIETTI.